United States Patent
Kahn et al.

(10) Patent No.: US 7,841,967 B1
(45) Date of Patent: Nov. 30, 2010

(54) METHOD AND APPARATUS FOR PROVIDING FITNESS COACHING USING A MOBILE DEVICE

(75) Inventors: Philippe Kahn, Aptos, CA (US); Arthur Kinsolving, Santa Cruz, CA (US)

(73) Assignee: DP Technologies, Inc., Scotts Valley, CA (US)

(*) Notice: Subject to any disclaimer, the term of this patent is extended or adjusted under 35 U.S.C. 154(b) by 0 days.

(21) Appl. No.: 11/740,887

(22) Filed: Apr. 26, 2007

Related U.S. Application Data (60) Provisional application No. 60/795,398, filed on Apr. 26, 2006.

(51) Int. Cl.
*A63B 71/00* (2006.01)

(52) U.S. Cl. .............................. 482/9; 482/8

(58) Field of Classification Search ............. 482/1–9, 482/901; 700/94; 463/1, 4, 6–7, 36; 434/236, 434/238, 247, 250, 255; 607/77; 705/2; 84/600, 612
See application file for complete search history.

(56) References Cited

U.S. PATENT DOCUMENTS

| | | | |
|---|---|---|---|
| 4,571,680 A * | 2/1986 | Wu | 377/24.2 |
| 4,776,323 A * | 10/1988 | Spector | 601/23 |
| 6,013,007 A | 1/2000 | Root et al. | |
| 6,478,736 B1 | 11/2002 | Mault | |
| 6,595,929 B2 | 7/2003 | Stivoric et al. | |
| 6,607,493 B2 * | 8/2003 | Song | 600/502 |
| 6,634,992 B1 | 10/2003 | Ogawa | |
| 6,672,991 B2 * | 1/2004 | O'Malley | 482/8 |
| 6,685,480 B2 * | 2/2004 | Nishimoto et al. | 434/247 |
| 7,254,516 B2 | 8/2007 | Case et al. | |
| 2002/0142887 A1 * | 10/2002 | O'Malley | 482/8 |
| 2003/0187683 A1 | 10/2003 | Kirchhoff et al. | |
| 2004/0219910 A1 | 11/2004 | Beckers | |
| 2005/0113649 A1 | 5/2005 | Bergantino | |
| 2005/0210300 A1 | 9/2005 | Song et al. | |
| 2006/0204214 A1 * | 9/2006 | Shah et al. | 386/54 |
| 2008/0153671 A1 * | 6/2008 | Ogg et al. | 482/3 |
| 2008/0214358 A1 * | 9/2008 | Ogg et al. | 482/9 |

* cited by examiner

*Primary Examiner*—Loan Thanh
*Assistant Examiner*—Sundhara M Ganesan
(74) *Attorney, Agent, or Firm*—Blakely, Sokoloff, Taylor & Zafman, LLP; Judith A. Szepesi (57) ABSTRACT

A method and apparatus providing fitness coaching including a mobile device to enable a user to receive a tailored fitness session.

20 Claims, 8 Drawing Sheets

METHOD AND APPARATUS FOR PROVIDING FITNESS COACHING USING A MOBILE DEVICE

RELATED CASES

The present application claims the benefit of U.S. Provisional Application Ser. No. 60/795,398, filed Apr. 26, 2006.

FIELD OF THE INVENTION

The present invention relates to a server to utilize integrated data from at least one health monitor, and more particularly to utilizing the health monitor data to create a fitness session.

BACKGROUND

NTT DoCoMo, Inc. is marketing the F672i (Raku Raku PHONE III) in Japan, the first mobile phone that also is a pedometer. The health phone records your steps, and it also can email them once a day to the address of the user's choice, or others can message the health phone with a specific subject line to find out your pedometer data. Given the high rates of both obesity and cell phone usage by teens in the US and Canada, adding a pedometer to cell phones could be a big public health benefit to encourage walking in the younger age groups.

However, this system provides very limited accountability, and no real-time data. Furthermore, there is no central data collection mechanism.

SUMMARY OF THE INVENTION

A method and apparatus providing fitness coaching. The system includes a cellular telephone designed to receive fitness coaching information from a server. The fitness coaching information, in one embodiment, includes music.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

The method and apparatus described is a mobile device which is designed to provide fitness coaching. In one embodiment, the mobile device may be a cellular telephone, or other mobile communication device which incorporates or is in communication with a server. In one embodiment, the mobile device may include a health monitor, such as a pedometer. In one embodiment, the system is a health phone that has a receiver to communicate with one or more external monitors, sensors, or devices (collectively referred to as SMDs). The SMDs may include a heart rate monitor such as a chest strap type monitor, for example. The health data, including the pedometer data and corresponding heart rate data are sent to the central server, in one embodiment. This is then used for fitness coaching and music selection, in one embodiment.

In one embodiment, the system includes a coach that reacts to the data from the health phone and reminds the user to maintain a certain level of activity throughout the day. The user may have the option, in one embodiment, to select the message type and frequency.

In one embodiment, the system may further include a sound output, such as a headset plug or microphone, and the ability to play music or other audio output. In one embodiment, the music may be a musical composition with words, a musical composition without words, or a rhythmic or polyrhythmic pattern. In one embodiment, the system may create and play lists of songs that can be attached to a walking program. In another embodiment, the system may enable the user to create such a play list. In one embodiment, the music—in this context the music corresponds to any rhythmic audio output which can be utilized to create a rhythm for body movement—may be customized for the user. In one embodiment, the system may include special music timed for the duration/steps/intensity of a predefined workout that one can download as part of the service. In one embodiment, the health phone service may include the built-in pedometer, a number of downloadable workouts, a number of songs, reporting and logging, ongoing alerts/alarms, encouragements, community participation, and life-style enhancement tips.

In one embodiment, the system may further include a sound output, such as a headset plug or microphone, and the ability to play music or other audio output. In one embodiment, the system may create and play lists of songs that can be attached to a walking program. In another embodiment, the system may enable the user to create such a play list. In one embodiment, the music—in this context the music corresponds to any rhythmic audio output which can be utilized to create a rhythm for body movement—may be customized for the user. In one embodiment, the system may include special music timed for the duration/steps/intensity of a predefined workout that one can download as part of the service. In one embodiment, the health phone service may include the built-in pedometer, a number of downloadable workouts, a number of songs, reporting and logging, ongoing alerts/alarms, encouragements, community participation, and life-style enhancement tips.

Cellular carriers, or third parties, may sell music and play lists to users to accompany their walks/fitness sessions. In one embodiment, users can specify music genres and beat speeds for their walk/run play lists and then download a play list to their mobile health phone optimized for a work out. In one embodiment, the beat speeds may be automatically adjusted/selected based on the user's fitness level and health monitor data. The system may create an entire play list tailored to the total workout time.

Furthermore, in one embodiment, the pace of each song/track in the play list could be tailored to an exact workout. For example, the tempo of the music could change in a way such that if the user keeps up with the pace, they exercise at precisely the optimal heart rate intervals for the goal that they are trying to achieve. This would be an easy and fun way to interval train. Instead of the user attempting to adjust workout speed and intensity, the music may simply provide the requisite information. In one embodiment, the data may be determined based on real-time health monitor data. For example, in one embodiment, the heart rate monitor may be coupled to the cellular phone so that the system may dynamically identify the optimal beat of the music to achieve a specific heart rate range in the user.

In one embodiment, this application can be applied to a user's existing play list. The application simply decides which songs should be played when to achieve an optimal workout. In one embodiment, the user may select genres, artists, musical types, etc. The system then selects from within the user's preferred set to match the fitness session.

In one embodiment, the system may insert verbal cues into the musical stream. These verbal cues may include encouragement, suggestions, corrections, and other coaching features.

In one embodiment, the system includes a set of songs whose beat is known. In one embodiment, the system includes a "music generator" that algorithmically generates music. Note that at its most basic, the tune, song, play list, or music may simply be a metronome like ticking which provides a beat for the user's fitness session.

Figure 1:
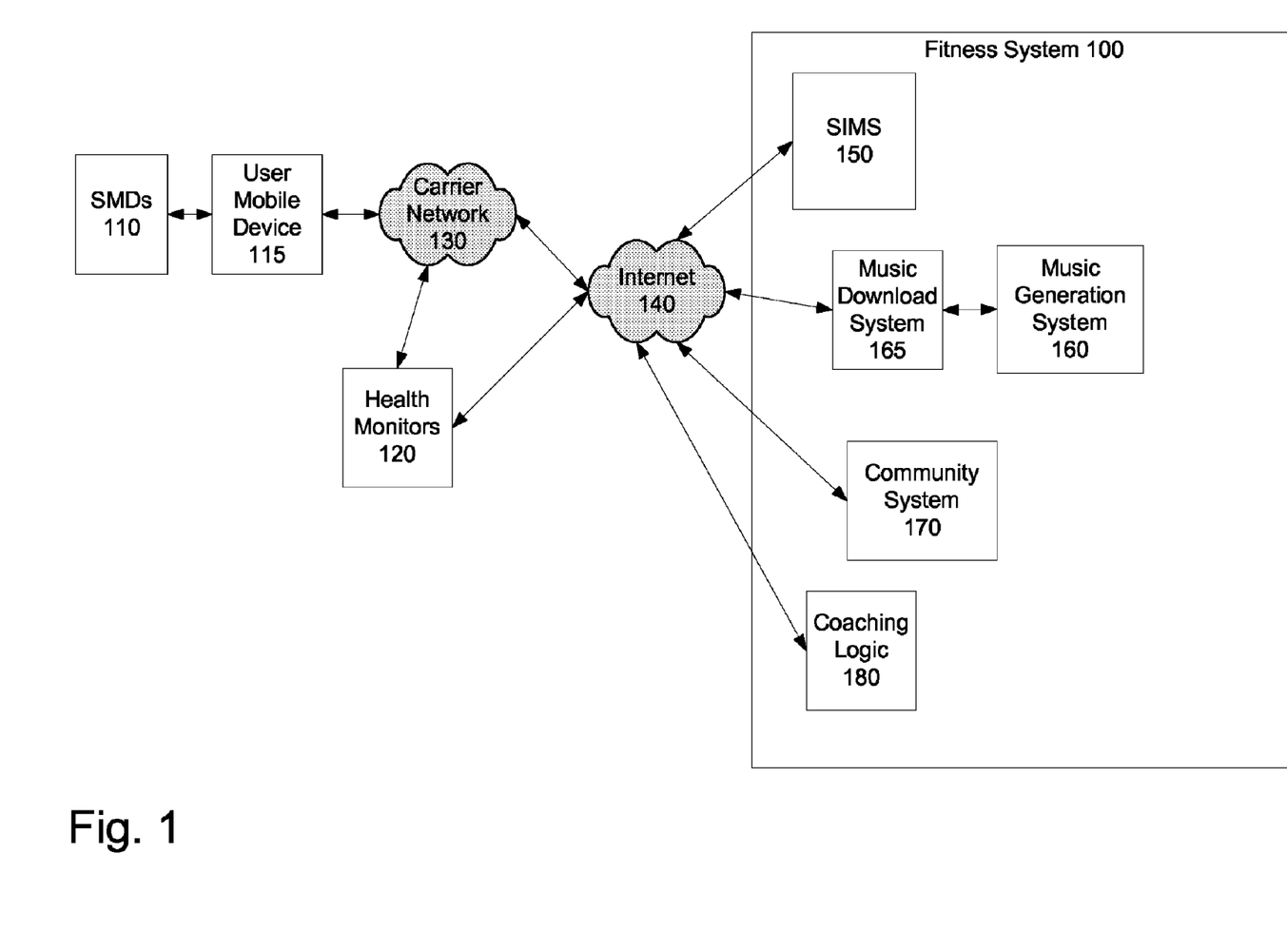
FIG. 1 is a block diagram of one embodiment of the network which may be used with the present invention.

FIG. 1 is a block diagram of one embodiment of the network which may be used with the present invention. The user's mobile device 115 may be a cellular phone, a wearable computer, or any other device which is generally carried by the user and provides connection to the Internet 140. In one embodiment, the user's mobile device 115 connects to the Internet 140 via carrier network 130. There may be a sensors, monitors, and/or devices (SMD) 110, 120 within the system. The SMDs 110, 120 may include various health devices such as heart rate, blood pressure, blood glucose level monitor, pedometer, etc. The SMDs may send their data to the user mobile device 115, or directly through carrier network 130 or Internet 140.

The health monitor and user device data is passed to fitness system 100. Fitness system 100 includes, in one embodiment SIMS 150, music generation system 160 and music download system 165, as well as community system 170, and coaching logic 180. In one embodiment, each of the elements of the fitness system 100 may be on a separate sever, or multiple servers. Alternatively, the elements may share a server or servers.

Figure 2:
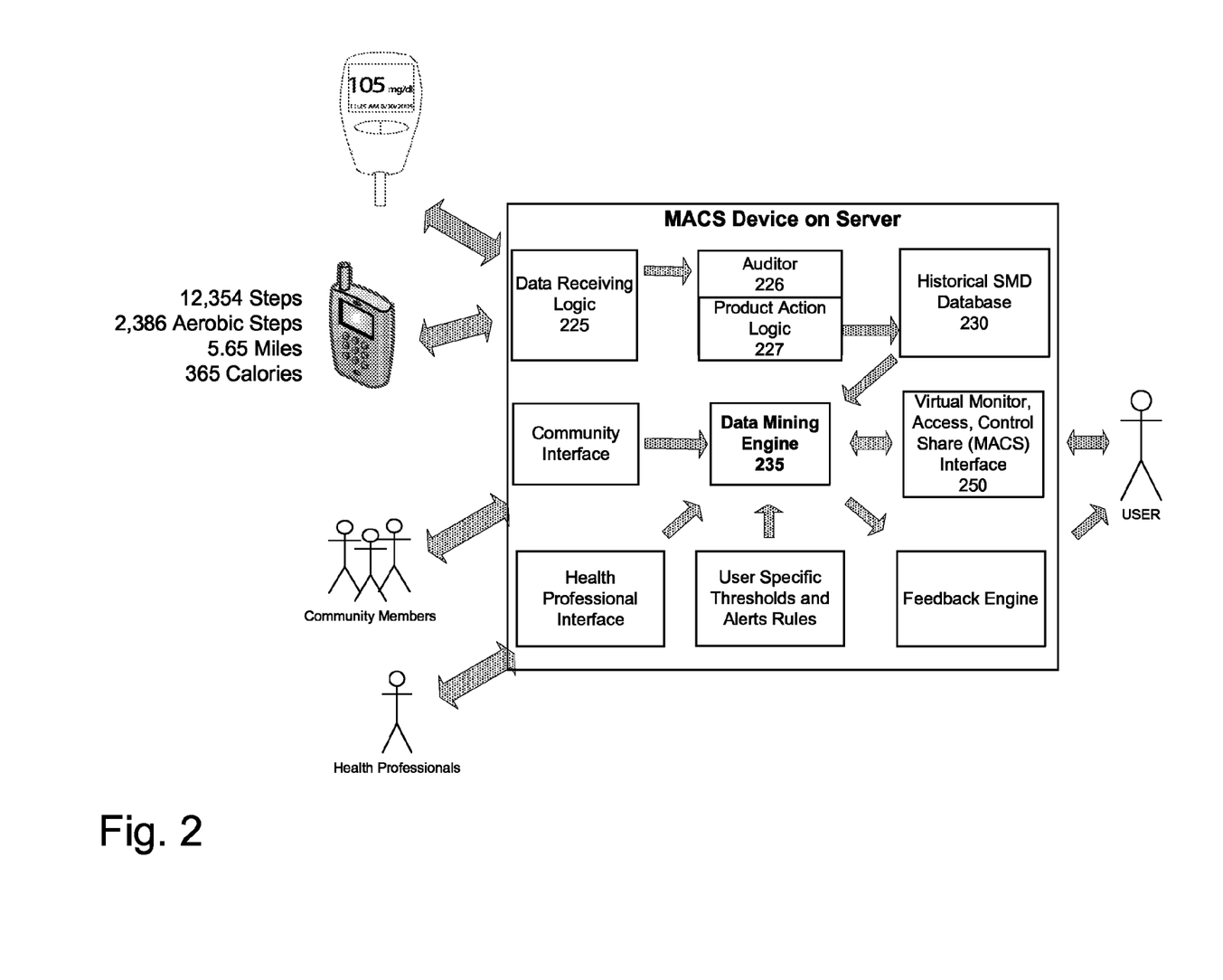
FIG. 2 is a block diagram of one embodiment of the MACS system.

FIG. 2 is a block diagram illustrating one embodiment of a Virtual Management, Access, Control, Share (MACS) device on the SIMS server and its relationship to the actual SMD. The actual SMD 210 has an intermittent connection 215 to a server 220. The connection 215 may be through the Internet, through a carrier network, or through other means. The server 220 may be located in the same location as the real SMD 210.

The data receiving logic 225 receives the data from the actual SMD 210 or the user via an intermittent connection 215. The data is stored in historical database 230. The historical data is used by data mining engine 235, to present virtual MACS device 250 via a reliable always-on connection 260 to various recipients 275. In a healthcare setting for example, the recipients may include the user, healthcare providers, and family.

In one embodiment, data mining engine 235 may further interface with user alerts and rules 240 to generate notifications through intelligent notification engine 255. Intelligent notification engine 255 can send automatic notifications to designated recipients 275, when certain threshold or alert conditions are met. The threshold or alert conditions may include historical data, trend analysis, variance from charted trends, simple threshold, or any combination of the use of historical and current data from the actual SMD 210, or combination of SMDs. In one embodiment, the data mining engine 235 constantly monitors the database 230, to ensure that the alert rules and user thresholds 240 have not been triggered. Intelligent notification engine 255 can, in one embodiment, trigger a notification in an appropriate format to any designated recipient.

In one embodiment, in addition to the database 230, data from other relevant actual SMDs may be received as well via logic 245. For example, in health setting, in addition to the glucose meter, exercise data, medical reports, and/or other relevant conditions may be monitored. The threshold and alert rules 240 may utilize a combination of data from more than one real SMD to trigger a notification or command 270.

Figure 3A:
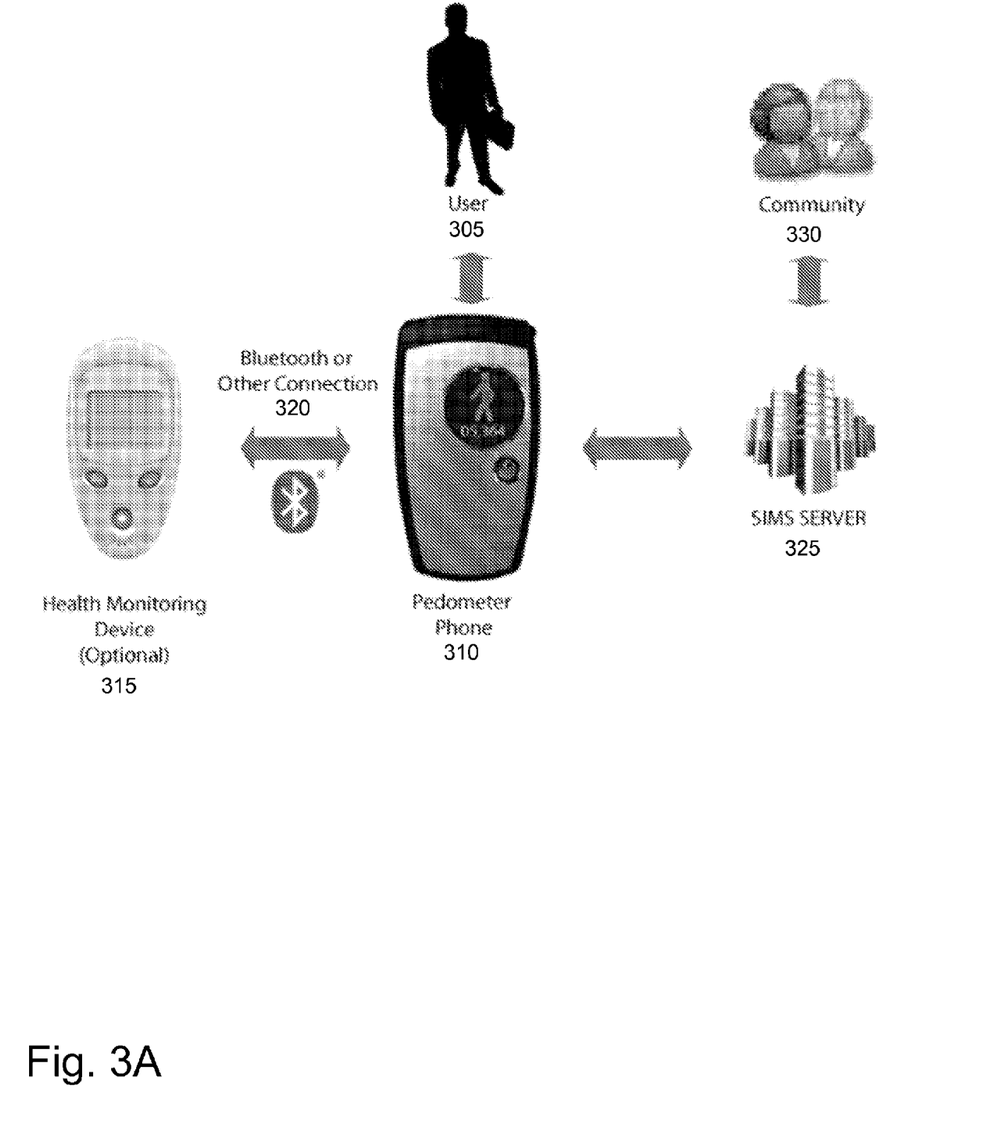
FIGS. 3A and 3B are exemplary sketches of the user system which may incorporate a health monitor and a mobile communications system.
Figure 3B:
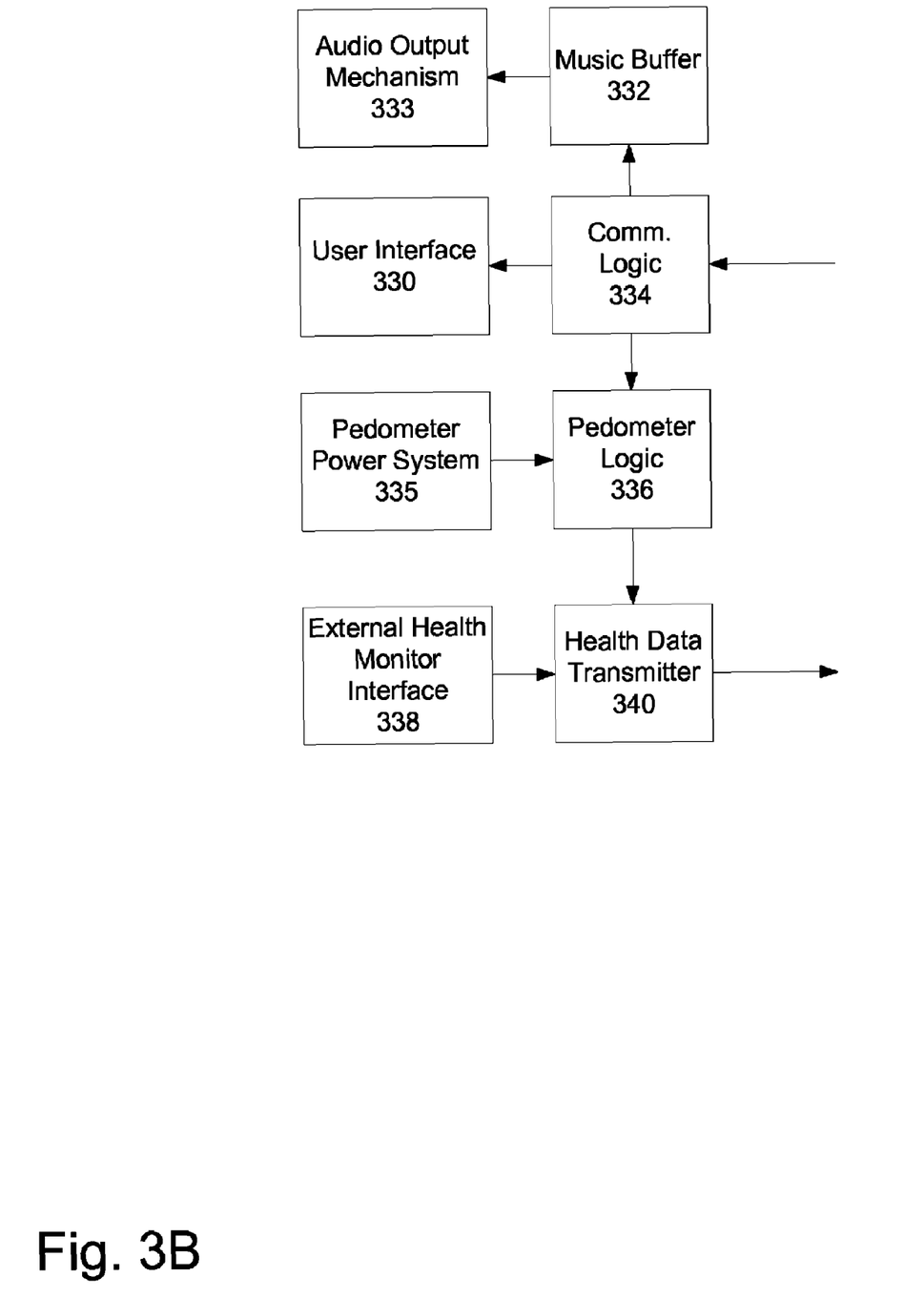

FIGS. 3A and 3B are exemplary sketches of the user system which may incorporate a health monitor and a mobile communications system.

FIG. 3A is a diagram of the client system elements. The health monitoring device 315 is coupled via Bluetooth or other connection 320 to health phone 310. Health phone 310 is carried by a user 305. The user's steps are tracked by health phone 310. The health phone 310 sends its data to SIMS server(s) 325. In one embodiment, health phone 310 sends its data via cellular network or via the Internet if it is a WAP enabled phone. In one embodiment, SIMS server 325 shares parts of the data, or analyzed data, with community 330. Community 330 is designed to provide encouragement to the user 310, to maintain a fitness regimen. In on embodiment, user 305 accesses community 330 on the World Wide Web, via a browser, or via health phone 310. The health phone 310 includes an audio output mechanism, which may include a speaker or a plug for a headphone or ear set. The fitness coaching mechanism in the health phone 310 in one embodiment provides music to the user for workouts.

FIG. 3B is a block diagram of one embodiment of the client system. The client system includes an activity monitor 336. In one embodiment, the activity monitor 336 is a pedometer. In one embodiment, the activity monitor 336 includes an accelerometer. The accelerometer may be a one, two, or three-dimensional accelerometer. In one embodiment, if the accelerometer is one or two-dimensional there may be two or more accelerometers that are part of the activity logic 336.

In one embodiment, the activity logic 336, which in one embodiment includes accelerometer and temporary data storage, is separately powered by activity monitor power system 335. The activity monitor power system 335 enables the activity monitor 336 to operate even when the client system (mobile telephone) is turned off.

The activity data from activity monitor logic 336 is transmitted to the server system via health data transmitter 340. In one embodiment, an external health monitor interface 338 is also included in the system. The external health monitor interface 338 is designed to receive health data from external health SMDs, such as glucose meters, heart rate monitors, etc. In one embodiment, external health monitor interface 338 is a Bluetooth interface, which is configured to receive health data from external health monitors. In another embodiment, external health monitor interface 338 may be a wired interface designed to receive a physically connected device. The data received via external health monitor interface is buffered, in one embodiment, and then passed on to health data transmitter 340.

In one embodiment, the health data is stored on the client system until health data transmitter 340 receives an acknowledgement that the data has been successfully received at the server (not shown). In one embodiment, a cyclic redundancy check (CRC) is included with the data, to ensure that the correct uncorrupted data was received by the server.

In one embodiment, the server may send feedback data to the health phone. The feedback data is received via communication logic 334. Communication logic 334, in one embodiment, passes feedback designed for the user to user interface 330. Feedback data, in one embodiment, may be text, audio data, or other types of data. In one embodiment, communication logic 334 may send some of the feedback data directly to activity monitor logic 336. For example, if the server determines that the accelerometer settings must be altered in some way, this data may be received from the server.

In one embodiment, the server may send workout music, or coaching data to the health phone. The data is received via communication logic 334. In one embodiment, music for a workout is sent as streaming data. In one embodiment, the health phone includes a music buffer 332. The music buffer 332 includes sufficient buffered content to ensure that playback is not interrupted by connection problems between the server and the health phone. In one embodiment, the music buffer 332 further includes an up-tempo and down-tempo variation on the music, to enable speedy adjustment if the user's workout is too vigorous or not sufficiently vigorous. In one embodiment, this is determined by the server, and feedback controlling such adjustments is received via the communications logic 334. In another embodiment, the health phone may make such an adjustment based on health rate data.

Figure 3C:
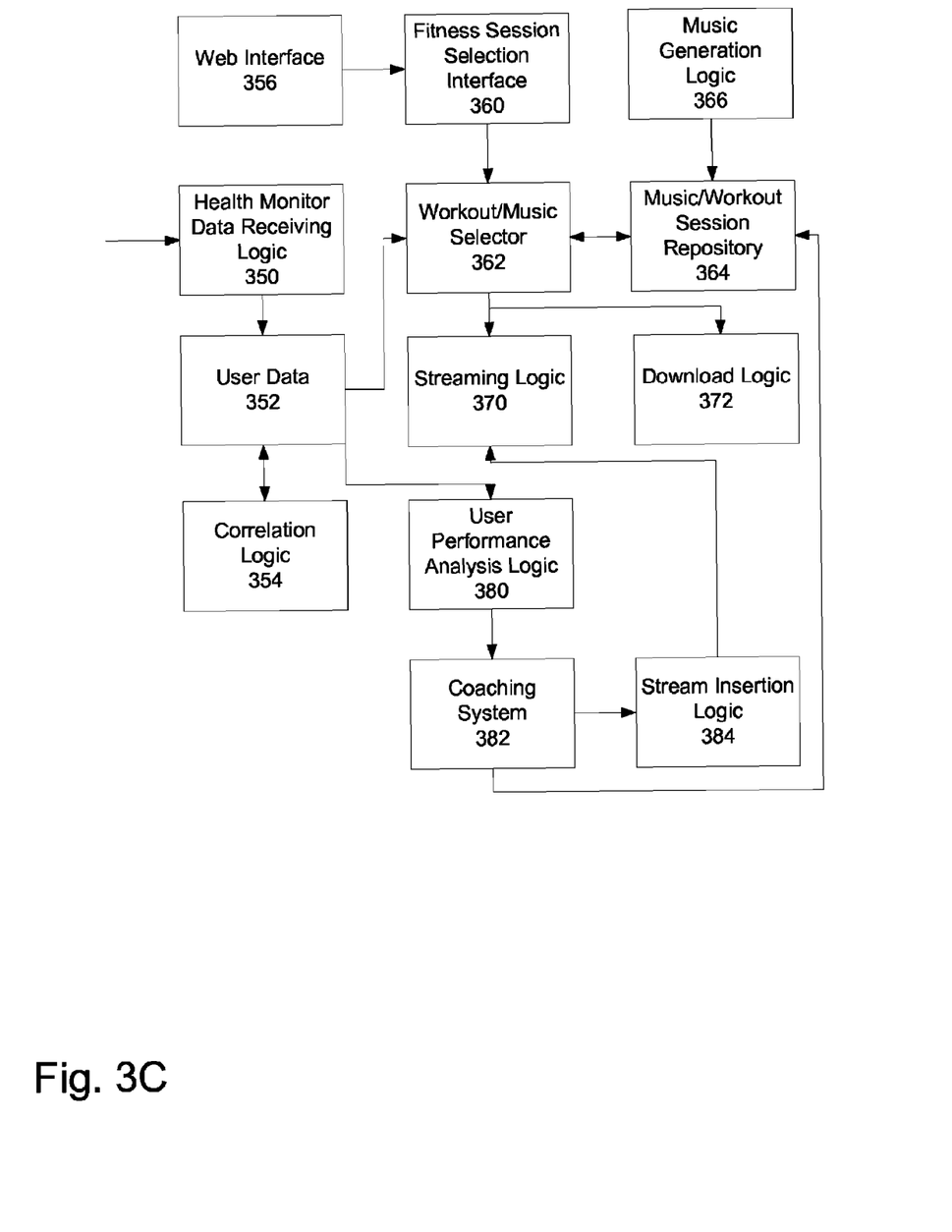
FIG. 3C is a block diagram of one embodiment of the server.

FIG. 3C is a block diagram of one embodiment of the server. Data is received from health phones, and potentially from external health monitors at data receiving logic 350. The data is stored as user data 352. In one embodiment, the user data 352 is analyzed, and the results of the analysis are also stored. In one embodiment, correlation logic 354 determines correlations between various measurements and behaviors.

The user can utilize a web interface 356 or an alternative interface, to access a fitness session selection interface 360. The interface may be accessible via the health phone. In one embodiment, the interface may be accessible via wireless access protocol (WAP), short messaging system (SMS), multimedia messaging system (MMS), or alternative methods.

Workout/music selector 362 enables a user to select a full workout, or one or more songs (units of music) for activities. The selector 362, in one embodiment, enables the user to select music by beats-per-minute, musical genre, artist, music type, musical attributes, or any other criteria or set of criteria. In one embodiment, repository 364 stores data about the available musical selections. In one embodiment, the beats-per-minute (BPM) of each musical selection are available as metadata. In one embodiment, for songs that change BPM during the song, the beats at each minute are stored as metadata. This enables the system to select musical selections for transitions as well. In one embodiment, the repository 364 may include musical segments as well. Musical segments include songs that are truncated because they include significant change in BPM/tempo, and generated songs.

Music generation logic 366 generates songs, in one embodiment, with a preset BPM, or transitions. In one embodiment, the music generation logic 366 generates music within a particular genre by using instrumentation from that genre. The generated songs are useful for transitions which may be hard to find in existing songs. In one embodiment, the generated songs may further be useful for users who do not wish to pay for the music they use with their workout. In another embodiment, generated music may also be priced equivalently to other downloadable songs.

Once the user has selected the workout or song(s), the system sends the music data to streaming logic 370 and/or download logic 372. In one embodiment, the user may select whether the song(s) should be streamed for immediate enjoyment or downloaded to the health phone. In one embodiment, the cost of the material may be based on whether the user is downloading it or streaming it.

The system further includes user performance analysis logic 380, in one embodiment. The user performance analysis logic 380 monitors the user data received via receiving logic 350. The user data 352 is correlated with the fitness session/music currently being played. If the user's health data indicates that he or she needs to slow down or speed up, the user performance analysis logic 380 sends the data to coaching system 382.

Coaching system 382 in one embodiment, updates the songs that should be streamed, to speed up or slow down the musical tempo. This is a fast way to adjust the intensity of a workout. In one embodiment, coaching system 382 furthermore notifies the user's system to switch to a buffered "slowing" or "speeding" track. This buffered track provides enough information to update the streamed or downloaded musical selection for the adjusted tempo.

In one embodiment, coaching system 382 further includes stream insertion logic 384, to insert verbal cues into the streamed music. The verbal cues may indicate transitions between workout phases, suggestions to alter some activity or motion, etc. In one embodiment, if the health phone is a pedometer phone which operates using one or more accelerometers, the coaching logic 382 may also analyze movement dynamics, and send messages such as "you seem to be favoring your right leg" or "your gait is becoming uneven," etc.

Figure 4:
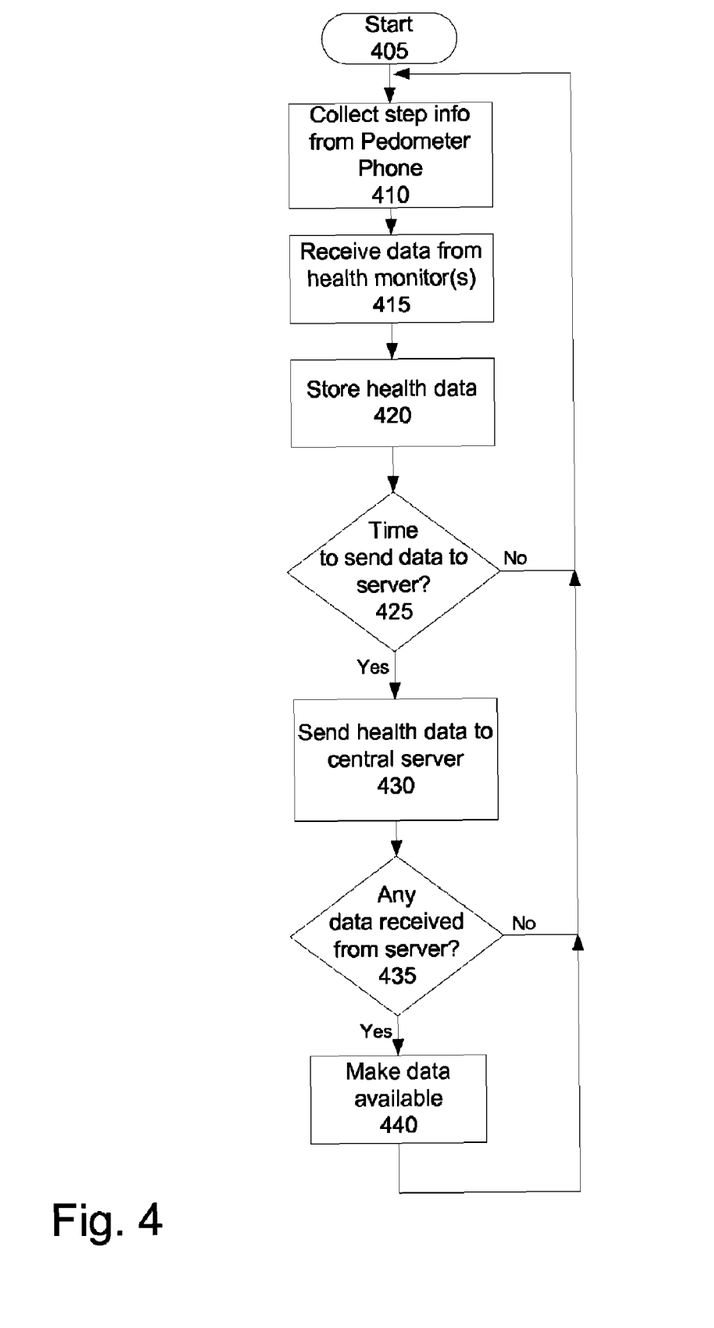
FIG. 4 is a flowchart of one embodiment of utilizing the health phone system including coaching.

FIG. 4 is a flowchart of one embodiment of the client-side process. This process is active whenever the user walks with the health phone (block 410). The health phone may receive data from other external health monitors as well. These external health monitors may include any monitors that can communicate with health phone, that are used to assess the user's current health status. For example, the health monitors may include a blood glucose monitor, a heart rate monitor, a blood pressure monitor, a blood oxygen level monitor, or any other type of health monitor. (block 415)

The health data is stored temporarily by the health phone (block 420). The process then determines whether it is time to send data to server (block 425). In one embodiment, the pedometer collects data continuously. In one embodiment, health monitors also may collect data continuously. The system, however, in one embodiment, only sends data periodically. If it is not yet time to send the data, the process returns to block 410 to continue collecting pedometer data. If it is time to send the data, the process continues to block 430.

In another embodiment, the data is stored in a buffer and immediately sent when received. In one embodiment, the pedometer data is stored separately by the pedometer aspect of the pedometer-phone, and only transmitted to the mobile-aspect of the pedometer-phone periodically, when it is immediately forwarded.

The data is sent to the central server (block 430). In one embodiment, the data may be sent as an email, SMS, via WAP, or in another format.

At block 435, the process determines whether any data has been received from the server. The server may return data to the user's health phone, in response to the data sent, or to cumulative data from the client, or other occurrences. The data may include music, coaching data, or alerts. If no data is received, the process returns to block 410 to continue collecting data.

If data is received, the data is made available to the user (block 440). In one embodiment, if the data is streamed music, the music is immediately sent to the output mechanism which may include a speaker, headset, or other output mechanism. If the data is downloaded music, in one embodiment, the music is stored on the client device. This music is then available to the user upon demand. If the data is an alert, the user is notified. In one embodiment, the system uses the standard SMS/email alerting system which is part of the health phone. Thus, the system itself need not do anything to alert the user. In one embodiment, the data received may be an adjustment to the health device, or something else that need not trigger a user alert. In that case, in one embodiment, the system need not trigger an alert. The process then returns to block 410, to continue collecting data.

Note that while this is described as a flowchart, these processes generally occur simultaneously. That is data is constantly collected, and whenever it is time, the data is sent. The system continuously monitors for data received from the server. The other flowcharts utilized in this application also may be executed in a non-linear order.

Figure 5:
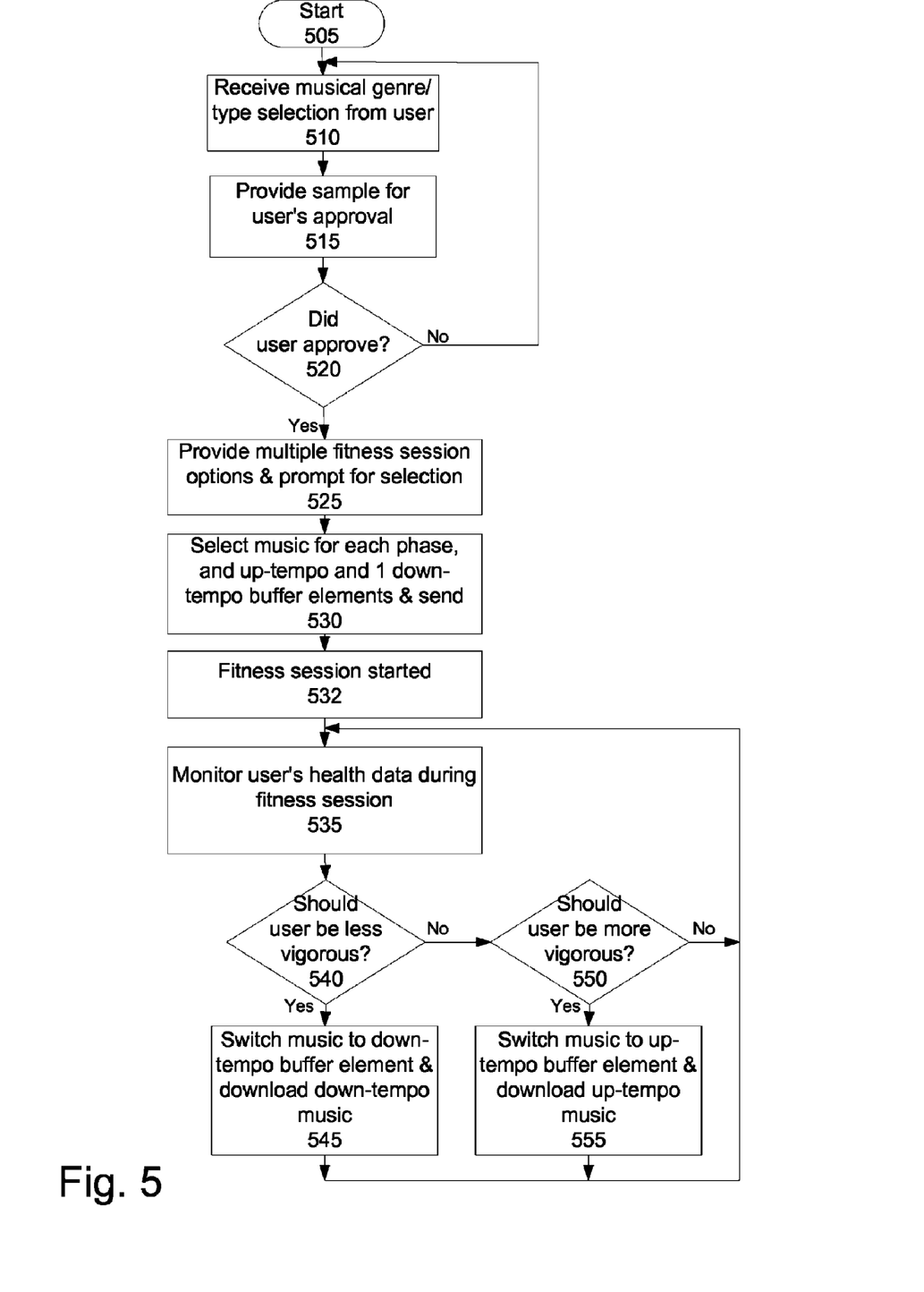
FIG. 5 is a flowchart of one embodiment of utilizing adjustable tunes for optimizing workouts.

FIG. 5 is a flowchart of one embodiment of utilizing adjustable tunes for optimizing workouts. The process starts at block 505. In one embodiment, blocks 510 through 530 occur prior to the fitness session. In one embodiment, the user may interact with the system through the user mobile device, in order to perform these set-up steps. In one embodiment, the user may interact with the system using a Web interface.

At block 510, the user selects a musical genre. In one embodiment, the user may instead enter a particular artist or song, and the genre may be determined based on that information. In another embodiment, the musical attributes are used instead of genres. In another embodiment, the system identifies analogous artists and/or songs and utilizes that instead of genres.

At block 515, a sample is provided for the user's approval, in one embodiment. This may be used to enable the user to adjust the selection, adjust output or format, or otherwise alter the audio. At block 520, the process determines whether the user approves, and if so continues to block 525. If the user does not approve, the process returns to block 510. In one embodiment, the user may, in addition to adjusting the genre/type, adjust output quality in various ways. These steps may be skipped, in another embodiment.

Once the user has approved, the process at block 525, provides one or more fitness session options, and prompts the user to select one. In general, a fitness session has multiple parts. For example, a fitness session may include warm-up, aerobic exercise, and cool-down sections. The length of the sections, in one embodiment, is adjustable by the user. For example, the user may select a 10 minute warm-up, 45 minutes of aerobic exercise, and 10 minutes of cool-down. In one embodiment, the fitness session may include aerobic exercise as well as weights, walking as well as running, etc. In one embodiment, the user may construct a fitness session to suit, from various available elements.

At block 530, the process selects the music for each phase of the fitness session. In one embodiment, the music selection has a beat-per-minute that is optimized for the users fitness level and the fitness session phase. In one embodiment, the music may be a number of songs in the user's genre. In one embodiment, one or more of the songs may be generated tunes. In another embodiment, the music may simply be a beat, similar to the beat generated by a metronome. The only requirement for the music is that it provides a beat which is designed to help the user maintain a particular level of movement. The songs, in one embodiment, are stored as a Musical Instrument Digital Interface (MIDI) file. In another embodiment, the music may be in Moving Pictures Experts Group 1 Layer 3 (MP3), Windows Media Audio (WMA), Ogg Vorbis, or Advanced Audio Coding (AAC) format. In one embodiment, for each distinctive segment, a "buffer element" is also selected. The buffer element enables a fast transition to a slower or faster pace by switching from the current song to the slower or faster song pre-downloaded as a buffer element. This ensures that there is no interruption in the session when the speed is changed. In one embodiment, the above steps are performed prior to the user initiating a fitness session, for example, when the user initially logs in.

At block 532, a fitness session is initiated. In one embodiment, the user may initiate a fitness session by selecting it from the mobile device. In one embodiment, the user may initiate the fitness session via an SMS, MMS, or locally by selecting it as an application on the user's mobile device. In another embodiment, the system may automatically initiate a fitness session if the user's activity level indicates that he or she has started a workout.

At block 535, the user's SMD data is received. The health monitor data may include one or more of the following: pedometer data, heart rate data, blood oxygen data, breathing speed data, blood pressure data, etc. This occurs while the fitness session is active, in one embodiment. In another embodiment, no feedback and analysis is available during the health session, because the health session does not include any health monitor data. In that embodiment, the process ends when the fitness session is initiated, at block 532.

At block 540, the process determines whether the user should be less vigorous based on the user's fitness level and SMD data. This may be determined based on heart rate, step cadence, blood oxygen level, or other health monitor data. If the user should be less vigorous, at block 545, the down-tempo buffer music is started, and the system downloads more music with the down-tempo cadence.

The process then continues to block 535, to continue monitoring the user's fitness session. In one embodiment, the process ends when the fitness session ends. In one embodiment, upon completion of a fitness session with a particular musical selection, the system downloads a next musical selection. In one embodiment, the next musical selection's tempo is selected based on information obtained during the fitness session. In other words, if the system determined that the user's fitness session was too vigorous, the subsequent selection will have a slower tempo, etc.

If the user was determined not to be too vigorous, the process at block 550 tests whether the session should be more vigorous. If so, the music is switched to an up-tempo buffer selection, and up-tempo music is downloaded. The process then continues to monitor, at block 535. If the user need not be more vigorous, the process also continues to block 535, to continue monitoring. In one embodiment, the monitoring process also is aware of the fitness session phase for the user. Thus, the user's optimal health monitor readings for each phase of a fitness session may be adjusted by utilizing musical cues.

Figure 6:
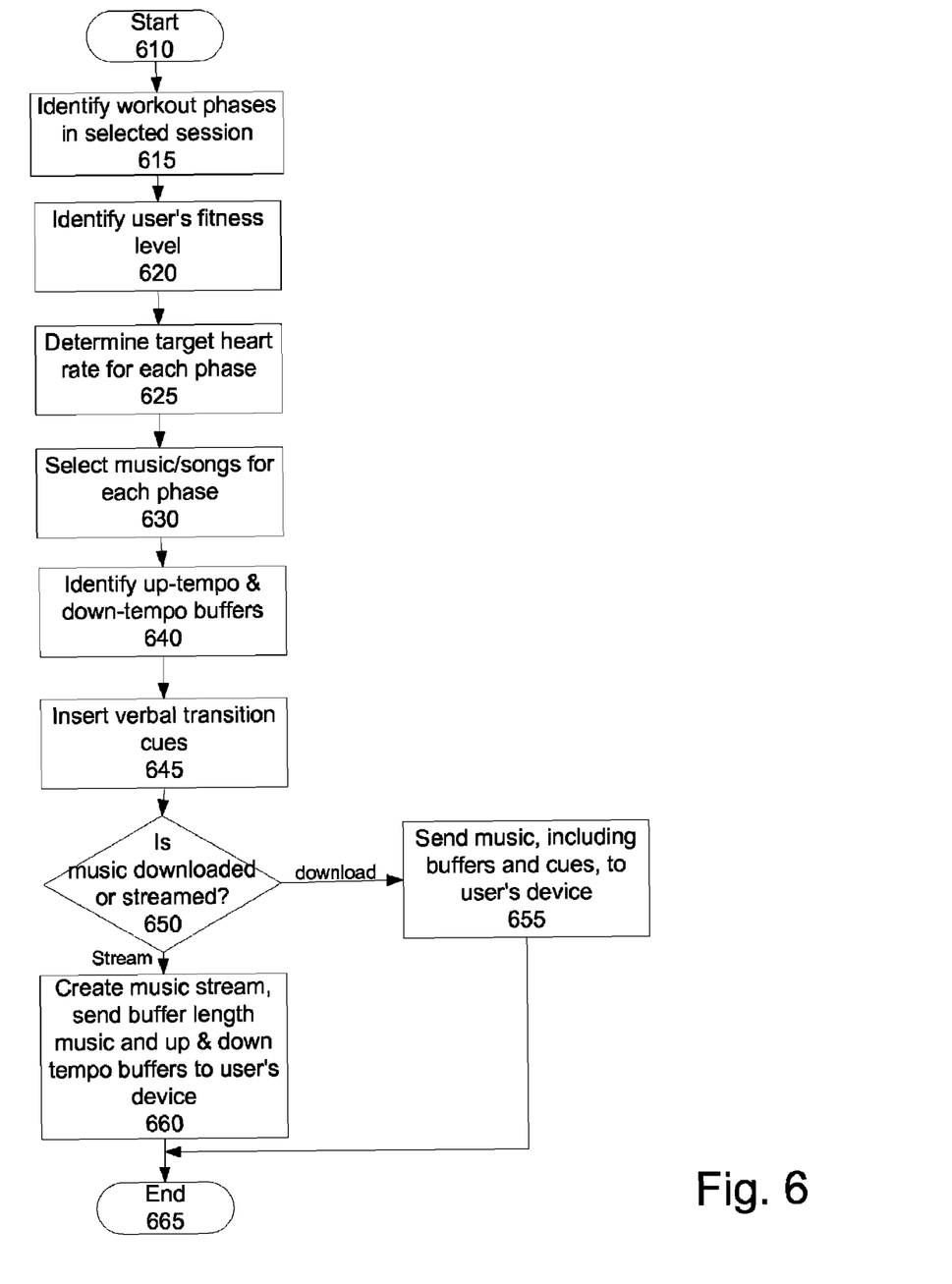
FIG. 6 is a flowchart of one embodiment of creating adjustable tunes including voice prompts.

FIG. 6 is a flowchart of one embodiment of creating adjustable tunes including voice prompts. The process starts at block 610. In one embodiment, this process starts when the user selects a fitness session, as described with respect to FIG. 5, block 525, above.

At block 615, the workout phases in the selected fitness session are identified. At block 620, the user's fitness level is identified. In one embodiment, the user's fitness level may be based on one or more of the following: age, gender, resting heart rate, known level of physical activity, historical performance in various fitness sessions, known medical conditions, and other medical or personal data which is available to the system. In one embodiment, the fitness level data is increased each time fitness session results are is obtained.

At block 625, the target heart rate for each phase of the fitness session is identified. Such calculations are known in the art.

At block 630, music is selected for each phase. As noted above, the music is selected to prompt the user to exercise to obtain the desired heart rate. In one embodiment, the beats-per-minute of the music is the determining factor.

At block 640, an up-tempo buffer song or snippet is identified, and so is a down-tempo song or snippet. The up-tempo snippet is designed to be pre-buffered, so that if the user should speed up, the system can immediately switch to the up-tempo piece, without waiting for download lag. Similarly, the down-tempo snippet is designed so that if the user's heart rate/health monitor indicators show that the user's heart rate is too high, the music can be immediately switched.

At block 645, in one embodiment verbal transition cues are inserted. In one embodiment, verbal transition cues are used to indicate to the user that the user should slow down, speed up, or change phase. For example verbal transition cues may be: slow down, your heart rate is too high; speed up, your cadence is too slow; transition from warm-up to aerobic phase, etc. In one embodiment, the user may select the verbal cues, and may opt to leave them out. In one embodiment, the verbal cues may be used to enable a full fitness session which resembles a fitness session with a personal trainer. For example, the cues may indicate when a user should switch from one machine to another, or from one workout element to another.

At block 650, the process determines whether the music is downloaded to the user's system or whether it is streamed. In one embodiment, if connectivity levels permit, the music may be streamed real-time (in one embodiment with buffering) to the user. In one embodiment, the cost to the user is different if the fitness session data is downloaded versus streamed. If the music is downloaded, the process at block 655 sends the music including buffers and cues to the user's device. In one embodiment, the user is prompted to trigger the download from the device. The process then ends at block 665.

If the music is streamed, the process at block 660 creates a music stream, and sends the pre-buffered portion and buffer-portions of the up-tempo and down-tempo transitions to the user's device. The buffering ensures that when the user indicates that a fitness session is starting, there is no lag even if the connection is slower than expected. In another embodiment, no buffering takes place, and the user may need to wait a few seconds for the pre-buffering when the fitness session is initiated. The process then ends at block 665.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A machine implemented method of providing a tailored fitness training session including music comprising:
enabling a user to set a musical genre preference;
creating an algorithmically generated song having a specific beat per minute profile;
generating a fitness training session including at least two phases, each phase having a different health goal;
upon initiation of a fitness training session, selecting from a set of songs within the musical genre including the one or more algorithmically generated songs, a sequence of songs based on the set musical preferences, the songs having an appropriate number of beats per minute for the phase of the fitness training session;
providing a musical cue to the user to transition between the first phase and the second phase of the fitness training session;
monitoring the user's health parameters during the fitness training session; and
adjusting the song selection to adjust the user's health parameters to an appropriate level for the current phase of the fitness training session.

2. The method of claim 1, further comprising:
inserting verbal cues for the user into the music.

3. The method of claim 1 further comprising:
streaming the songs during the fitness training session; and
pre-storing buffer music to enable a smooth change in tempo for adjusting of the song selection based on the user's health parameters.

4. The method of claim 1, wherein the cue is one of: a verbal cue, the musical cue, or the verbal cue in addition to the musical cue to transition the fitness training session.

5. The method of claim 1, wherein the music is presented in a format selected from among: MID1, MP3, WMA, Ogg Vorbis, and AAC.

6. The method of claim 1, wherein the song comprises: a musical composition with words, a musical composition without words, a rhythmic or polyrhythmic pattern.

7. The method of claim 1, further comprising:
tracking a number of steps per minute and verifying that the number of steps corresponds to an appropriate fitness training session level.

8. The method of claim 1, wherein the algorithmically generated song provides a smooth transition from a first song having a first beat per minute to a second song having a second beat per minute.

9. The method of claim 1, further comprising:
downloading an initial portion of the sequence of songs; and
downloading an up-tempo buffer and a down-tempo buffer to enable instantaneous change in the tempo to adjust the song selection to adjust the user's health parameter.

10. The method of claim 9, further comprising:
streaming the sequence of songs; and
playing one of the up-tempo buffer or the down-tempo buffer to enable pre-buffering of a new sequence of songs when the song selection is adjusted in response to the user's health parameter.

11. A machine-implemented method of providing a tailored fitness training session comprising:
generating a fitness session by a fitness system on a computing device, the fitness session including at least two subparts having different goals;
automatically selecting a sequence of songs for each of the subparts of the fitness session by the fitness system, the sequence of songs maintaining an appropriate number of beats per minute, based on the goal of the subpart;
providing a cue to the user to transition the user from a first subpart to a second subpart;
monitoring the user's health parameters during the fitness training session; and
adjusting the song selection to adjust the user's health parameters to an appropriate level for the current subpart of the fitness training session.

12. The method of claim 11, further comprising:
inserting verbal cues for the user into the music.

13. The method of claim 11, wherein the cue to transition the fitness training session between the subparts comprises one of: a verbal cue, a musical cue, and a combination of a verbal cue and musical cue.

14. The method of claim 11, wherein the song comprises: a musical composition with words, a musical composition without words, a rhythmic or polyrhythmic pattern.

15. The method of claim 11, further comprising:
algorithmically generating a song with an appropriate number of beats per minute for the tailored fitness session, the song being in a genre specified by the user's musical preferences.

16. A machine implemented method comprising:
generating a fitness session on a computing device, the fitness session including at least two subparts having different goals;
selecting a sequence of songs for a subparts of the fitness session, the sequence of songs maintaining an appropriate number of beats per minute, based on the goal of the subpart;
algorithmically generating a song to transition between subparts of the fitness session, the algorithmically generated song designed to smoothly move the user's heart rate from a first rate to a second rate and providing a musical cue to transition the user between the subparts of the fitness session.

17. The method of claim 16, further comprising:
inserting verbal cues for the user into the music.

18. The method of claim 16, wherein the cue to transition the fitness training session between the subparts comprises one of: a verbal cue, a musical cue, and a combination of the verbal cue and musical cue.

19. The method of claim 16, wherein the algorithmically generated song is in a genre specified by the user's musical preferences.

20. The method of claim 19, wherein the algorithmically generated song comprises: a musical composition with words, a musical composition without words, a rhythmic or polyrhythmic pattern.

* * * * *